United States Patent [19]
Kaiser

[11] Patent Number: 4,808,930
[45] Date of Patent: Feb. 28, 1989

[54] TECHNIQUE OF COMPENSATING FOR CAPACITIVE EFFECTS IN CONDUCTIVITY MEASUREMENTS

[75] Inventor: Donald F. Kaiser, Parsippany, N.J.

[73] Assignee: Beckman Industrial Corporation, Cedar Grove, N.J.

[21] Appl. No.: 903,388

[22] Filed: Sep. 3, 1986

[51] Int. Cl.$^4$ .................. G01N 27/48; G01R 27/22
[52] U.S. Cl. .................. 324/442; 324/441; 324/439; 204/406
[58] Field of Search .............. 324/438, 439, 440, 441, 324/442, 443, 444, 60 R; 204/293, 400, 406, 407

[56] References Cited

U.S. PATENT DOCUMENTS

| | | | |
|---|---|---|---|
| 3,644,824 | 2/1972 | Barker et al. | 324/440 X |
| 3,919,627 | 11/1975 | Allen | 324/442 X |
| 4,132,944 | 1/1979 | Bentz | 324/441 X |
| 4,337,434 | 6/1982 | Fogel et al. | 328/114 |
| 4,516,077 | 5/1985 | Fenneman et al. | 324/425 |
| 4,656,427 | 4/1987 | Dauphinee | 324/444 |
| 4,682,113 | 7/1987 | Barben | 324/441 |
| 4,683,435 | 7/1987 | Blades | 324/442 |

OTHER PUBLICATIONS

Van Norstrand's Scientific Encyclopedia, Sixth Edition, "Integrating-Ramp A/D Converter."
"Journal of Chemical Education", Braunstein et al., vol. 48, No. 1, Jan. 1971, pp. 52-59.

Primary Examiner—Roy N. Envall, Jr.
Assistant Examiner—H. L. Williams
Attorney, Agent, or Firm—Kinney & Lange

[57] ABSTRACT

Improved accuracy in solution conductivity or resistivity measurment uses a center-sampling technique in which an AC drive is applied to a conductivity cell and the conductivity cell voltage is sampled during a predetermined time interval in the center of a half cycle drive waveform. The effects of cell capacitance, and particularly the electrode-solution capacitive, are compensated by periodically sampling during a second time interval which is different from the first interval. Based upon the difference between the sampled voltages in the first and second intervals, a correction to the measured conductivity or resistivity is made to compensate for capacitance induced errors.

14 Claims, 8 Drawing Sheets

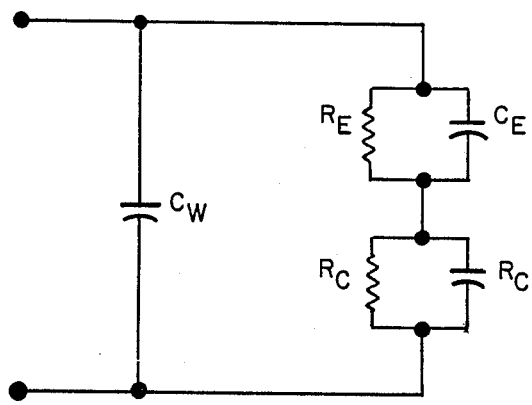
$C_W$: INTER-LEAD CAPACITANCE FOR CABLE CONNECTING THE CELL TO THE DRIVER ELEC.
$R_E$: ELECTRODE-SOLUTION INTERFACE RESISTANCE.
$C_E$: ELECTRODE-SOLUTION INTERFACE CAPACITANCE.
$C_C$: CELL INTER-ELECTRODE CAPACITANCE
$R_C$: K x P  WHERE  K = CELL CONSTANT
              P = SOLUTION RESISTIVITY
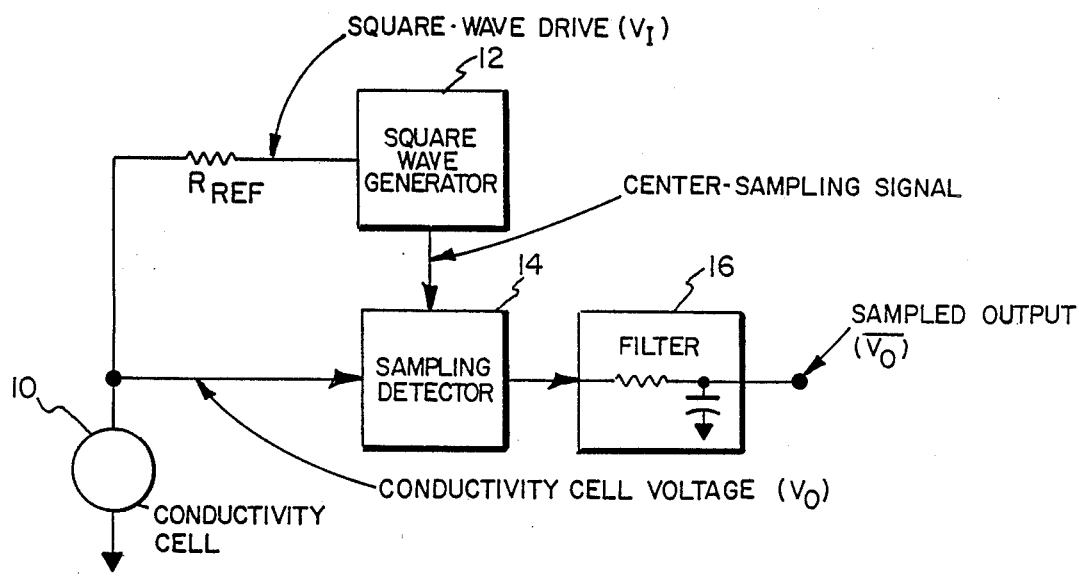
*Fig. 2*
PRIOR ART

TECHNIQUE OF COMPENSATING FOR CAPACITIVE EFFECTS IN CONDUCTIVITY MEASUREMENTS

BACKGROUND OF THE INVENTION

1. Field of the Invention

The present invention relates to measurement of conductivity (or resistivity) of a solution using a conductivity cell with conductive electrodes.

2. Description of the Prior Art

The measurement of solution conductivity or resistivity is used in a wide variety of applications throughout the process control industry. In particular, the conductivity or resistivity of water may be monitored as an indicator of purity. Absolutely pure water measures approximately 18.25 megohm-centimeters (Meg-cm) resistivity at 25.0° C. Ionic contaminants, most commonly salts, reduce the resistivity of a water sample below this theoretical maximum. A water sample sufficiently free from ionic contaminants that its resistivity is 5 megohm-centimeters or greater is commonly referred to as "high purity" or "ultra pure" water.

Certain industries prefer to measure water purity in terms of conductivity, the mathematical inverse of resistivity. Conductivity is commonly measured in terms of micro mhos/centimeter ($\mu$mho/cm) or micro Siemens/centimeter ($\mu$S/cm) the units being equivalent, ultra pure water may be described as having a conductivity of 0.2 micro Siemens/centimeter or less.

Conductivity or resistivity of aqueous solutions is typically measured by immersing two conductive surfaces, held in fixed relation to each other, into the solution in question. An electric current is made to flow between the surfaces, through the solution. Assuming the surfaces are themselves perfect conductors, are in perfect electrical contact with the solution, and that the electrical current does not effect the nature of the solution, the solution's conductivity may be calculated as:

$$\text{Resistivity } \rho = \frac{Vc}{Ic\,K} \qquad \text{Eq. 1}$$

$$\text{Conductivity } \sigma = \frac{1}{\rho} = \frac{K\,Ic}{Vc} \qquad \text{Eq. 2}$$

Where:
$Ic$=Electric current flowing between the conductive surfaces.
$Vc$=Voltage across the surfaces.
$K$="Cell" Constant describing the size and separation of the conductive surfaces.
For flat parallel surfaces of area A and separation L with conductive solution only between the plates, $K=L/A$. Hence the units megohm-centimeters for resistivity, micro mhos/centimeter for conductivity. The geometrically fixed conductive surfaces, or electrodes are collectively referred to as a conductivity cell.

This basic form of a conductivity cell immersed in a liquid may be electrically modeled as a simple resistor $R_C$ with value equal to the product of solution resistivity $\rho$ and cell constant K.

For reasons of convenience, modern conductivity cells generally consist of two concentric cylindrical electrodes. An insulating material supports the electrodes and maintains their fixed geometry. Often a temperature monitoring device (RTD or thermistor) is placed in contact with one of the electrodes for purposes of monitoring the temperature of the solution in which the cell is immersed.

A wide variety of conductive materials, ranging from graphite to various types of corrosion resistant steels, are used to make up conductivity cell electrodes. Similarly, a wide variety of materials including glass and epoxy, are used to make up those insulating parts of the cell which hold the electrode geometry fixed. Various minor variations on the concentric cylinder geometry and even some parallel plate electrode configurations are used to ensure a reliable circulation of sample solution in the cell.

All conductivity cells involving electrodes which contact the sample solution, regardless of geometry or material, share the same basic model and the same shortcomings and limitations.

The simple conductivity cell model described above is not adequate for the majority of real-world conductivity measurement applications, particularly where high purity water measurement is involved.

Several problems limit the accuracy of the simple model, the most significant of these being polarization. Polarization is the result of chemical activity between the electrode and solution in the presence of the electrical current used to make the conductivity measurement. A voltage potential, Vcell, must be added to the simple cell model (in series with the resistance) in order to account for polarization effects.

The crux of the polarization problem is that it is nearly impossible to characterize for any real-world application. The magnitude of Vcell is a function of a number of variables including: the electrical current flowing through the cell, temperature, time, electrode material, and solution chemistry. The last of these variables is always an unknown in practical applications, or it would be unnecessary to make the conductivity measurement in the first place.

In short, the error introduced by polarization in such simple conductivity measurement schemes is also virtually impossible to characterize. For this reason, all but the most crude of conductivity measurement schemes employ a somewhat more sophisticated measurement technique.

Virtually all modern conductivity measurement systems now operate their conductivity cells with an alternating current drive signal, in place of a simple direct current drive. Conductivity cells are driven at frequencies ranging from 50 to 60 Hz up to several kHz and at low current levels, typically under 100 micro-amperes. Since the error voltage due to polarization is a direct function both of electrical current magnitude and of the length of time during which current is applied to the conductivity cell, a measurement technique using an alternating current electrical drive of limited magnitude does indeed serve to reduce the error due to polarization.

Although it limits error due to polarization, an alternating current conductivity measurement scheme brings with it new sources of error. Specifically, the capacitive components of the conductivity cell must now be considered. In particular, the inter-lead capacitance $C_W$ for connecting the cell to driver electronics, the electrode-solution interface capacitance $C_E$, the cell interelectrode capacitance $C_C$, and the electrode-solution interface resistance $R_E$ all have an effect on the cell voltage.

Typical values for a common 0.01 cell constant conductivity cell according to the circuit in FIG. 1 in a high purity water application are as follows:

$C_W$ = 30 picofarads/ft × cable length

≦ .002 microfarads (cable length ≦ 50 ft.)

$R_E$ ≃ 200,000 ohms $C_C$ = 80 $\epsilon_o/K$ for acqueous solutions

≃ 600 picofarads 50,000 ohms ≦ $R_C$ ≦ 183,000 ohms for high purity water at 25° C.

Empirical studies indicate that for high purity water, $C_E$ is not a constant, but is related to the resistivity of the measured solution, and the available surface area of the cell electrodes.

For example, a currently available "glass" conductivity cell with constant K=0.01 and platinum electrodes plated with highly porous platinum black, provides $C_E$>1 microfarad in solution with $\rho$=18.3 megohm-cm. Another electrode employing titanium-palladium electrodes, popular with industrial users for its durability, provides $C_E$≃0.1 microfarad in the same solution.

The effects of all resistance and capacitance components of the conductivity cell model must be considered in order to obtain the maximum accuracy in the measurement of solution conductivity or resistivity.

The majority of conductivity measurement systems currently on the market do not address the conductivity cell error terms $C_W$, $C_C$, $C_E$ and $R_E$. Rather, the conductivity cell is treated as the simple model (i.e. only resistance $R_C$) and the neglected error terms are allowed to remain present in the system conductivity or resistivity output display.

In general, the error induced by $C_W$, the cable interlead capacitance, may be limited by limiting the length of cable recommended for use in connecting the conductivity cell to the system drive and measurement electronics. In addition, some systems provide a gain adjustment as part of the measurement electronics. Such an adjustment may be used to calibrate the conductivity measurement system at one point, but does little to improve system accuracy over a broad range of conductivity or resistivity values.

The most sophisticated of presently available conductivity measurement systems employ a "center-sampling" technique to reduce the effects of the previously described error terms. To employ this technique, the conductivity cell is driven with a square-wave signal in the 50 to 1,000 Hz range. Alternatively, a trapezoidally shaped drive waveform may be used with similar results.

Cell voltage waveform is the resultant voltage across the conductivity cell when the square wave drive signal is placed across the cell through a reference resistor $R_{REF}$. If the conductivity cell were a purely resistive device, the conductivity cell voltage would be a simple square wave with magnitude, V0:

$$\overline{V_O} = V_{DRIVE} \frac{K \cdot \rho}{R_{REF} + K \cdot \rho} \qquad \text{Eq. 3}$$

Because of the effects of the cell capacitance terms, most significantly $C_W$ and $C_E$, the cell output voltage waveform is distorted. The effects of $C_W$ are significant during the early part of the waveform where it causes a non-zero risetime in the conductivity cell output voltage waveform.

The effects of $C_W$ may be essentially eliminated by (a) limited cable length such that $C_W$'s time constant is much less than $\tau/8$ (where $\tau$ is the period of one cycle of the drive waveform), and (b) "center-sampling" the cell output voltage waveform. Center-sampling is achieved by generating a logic signal which is active only between times $\tau/8$ and $3\tau/8$, the center of the positive half-waveform. The sampled voltage is defined only during the sampling interval, $\tau/8 \leq$ time $\leq 3\tau/8$.

Since $C_W$'s time constant is kept short, its effects are negligible by time $\tau/8$ when the sampling interval begins. By averaging the cell voltage output only between times $\tau/8$ and $3\tau 8$, the effects of $C_W$ are kept to negligible levels.

Center-sampling also reduces, but does not eliminate, the effects of $C_E$ on the measured cell output. For most applications the drive frequency is chosen such that:

$$|Z_C| = \frac{1}{2\pi f C_E} << R_E \qquad \text{Eq. 4}$$

and the effects of $R_E$ can be ignored.
From the model it is derived that:

$$\overline{V_O} = \underbrace{\frac{V_{IM}R_C}{(R_C + R_{REF})}}_{\text{Ideal Term}} + \underbrace{\frac{V_{IM}R_{REF}}{(R_C + R_{REF})} - \frac{8V_{IM}C_E/R_{REF}}{1 + e^{\frac{-1}{2fC_E(R_C+R_{REF})}}} \times \left[ e^{\frac{-1}{8fC_E(R_C+R_{REF})}} - e^{\frac{-3}{8fC_E(R_C+R_{REF})}} \right]}_{\text{ERROR TERM}} \qquad \text{Eq. 5}$$

Where:
$\overline{V_O}$=Average cell output voltage sampled between $\tau/8$ and $3\tau/8$.
$R_{REF}$=Reference resistor
$R_C = K \times \rho$
$V_{IM}$=Magnitude of the square wave drive signal If the effects of $C_E$ are neglected ($C_E$ assumed to be infinitely large), the error term disappears, the model reduces to that of the simple cell, and the solution resistivity may be calculated from the measured quantity, $V_0$, and the known values for K, $R_R$, and $V_{IM}$.

This technique Works quite well assuming the effect of $C_E$, as reduced by the center-sampling technique, actually is negligible.

This is generally the case for cells using platinum electrodes plated with platinum-black. Such cells, because of their high electrode surface porosity, exhibit large $C_E$ values. This reduces the error term to a level which is, for most cases, insignificant.

Platinum/platinum-black electrodes, however, are too fragile to be suitable for most industrial applications. Cells using electrodes made of tough alloys, such as titanium-palladium, are favored by industrial users for their resistance to both physical and chemical attack.

This type of electrode is much less porous, and exhibits a much lower $C_E$ value than a comparable platinum/platinum-black electrode. In addition, as the cell is used, the electrodes often become covered with precipitate from the measured solution. This tends to reduce the value of $C_E$, and hence increases the error term of Equation 5 still further.

In actual use, conductivity cells using titanium-palladium electrodes may introduce errors of up to one percent into the resistivity or conductivity measurement system when new. This error value may increase undetected to five percent or more over the life of the conductivity cell, as precipitate gradually forms on the cell electrodes. A five percent error is undesirable in most applications and unacceptable in many.

SUMMARY OF THE INVENTION

The present invention is an improved method and circuit for providing an output which is representative of conductivity (or resistivity) sensed by a cell. The present invention is based upon the recognition that capacitive effects must be corrected for in order to achieve higher accuracy in the measurements made by a conductivity cell.

With the present invention, the cell receives an alternating excitation, and the cell output is sampled during two separate time intervals during which capacitance associated with the cell has two different effects. Based upon the difference in the output signals sampled during the first and second time intervals, the output based upon the sample value during the first time interval is corrected for the effects of capacitance.

In preferred embodiments of the present invention, the first time interval is a center-sampling time interval, while the second interval is an end-sampling time interval.

BRIEF DESCRIPTION OF THE DRAWINGS

FIG. 1 is an electrical schematic diagram of a model for a conductivity cell driven with an alternating current drive signal.

FIG. 2 is a block diagram of a prior art center-sampling conductivity measurement system.

DETAILED DESCRIPTION OF THE PREFERRED EMBODIMENTS

As discussed above, and modeled in FIG. 1, an industrial-type conductivity cell cannot be accurately modeled as a simple solution conductivity dependent resistor. The effects of cable inter-lead capacitance $C_W$, electrode solution resistance and capacitance $R_E$ and $C_E$, respectively, and cell inter-electrode capacitance $C_C$ must be accounted for.

Figure 3:
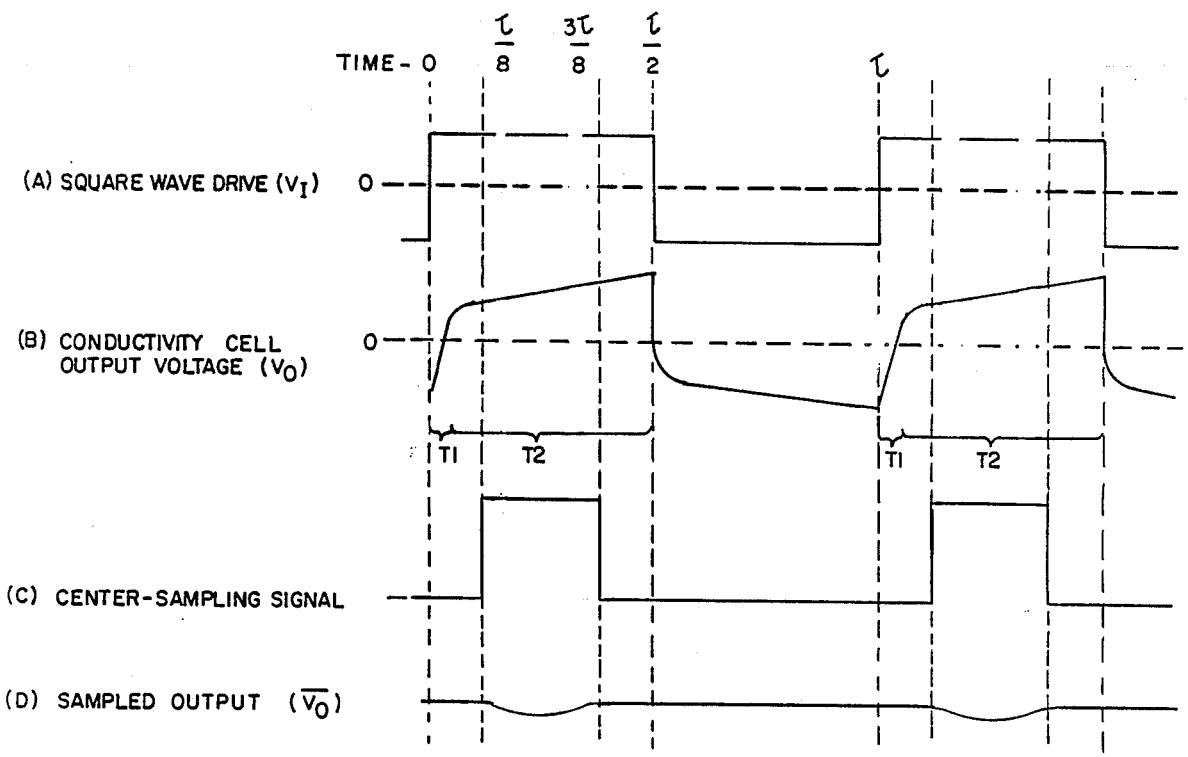
FIG. 3 shows waveforms produced by the prior art center-sampling conductivity measurement system of FIG. 2.

As discussed above, a center-sampling technique can reduce the effects of inter-lead capacitance. FIG. 2 is a block diagram showing a typical center-sampling conductivity measurement system. In FIG. 2, a conductivity cell 10 receives a square wave alternating current (AC) drive signal $V_I$ from square generator 12 through reference resistor $R_{REF}$. The conductivity cell voltage $V_0$ is supplied to sampling detector 14. Square wave generator 12 also produces a center-sampling signal which causes sampling detector 14 to sample the conductivity cell voltage $V_0$ during a time interval from time $\tau/8$ to $\tau 8$. The output of sampling detector 14 is filtered by filter 16 to produce a sampled output $\overline{V_0}$. FIG. 3 shows the waveforms produced by the prior art center-sampling conductivity measurement system of FIG. 2.

By using a center-sampling technique and limiting cell cable length, it is possible to reduce the value of the cable inter-lead capacitance $C_W$ to the point where it can be eliminated from the model as an error source. The cell inter-electrode capacitance $C_C$ can be eliminated by similar arguments. Its magnitude, typically less than about 700 picofarads for cell constants $K=0.01$ or greater in aqueous solutions, is small enough with respect to $C_W$. Its effect on system error is also made negligible by the use of a center-sampling technique. As also discussed above, the electrode-solution resistance $R_E$ is effectively short-circuited by the electrode solution capacitance $C_E$ in most applications. Thus, $R_E$ is eliminated as a source of error.

Figure 4:
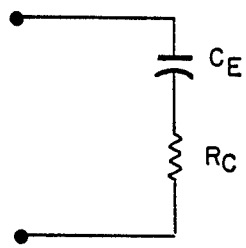
FIG. 4 is a simplified conductivity cell model for high purity water measurements.

This leaves the simplified conductivity cell model of FIG. 4, appropriate to high purity water applications, where the center-sampling technique is carefully applied. This model includes only capacitance $C_E$ in series with $R_C$ between the cell terminals.

A typical conductivity measurement for high purity water might employ a $K=0.01$ constant cell, driven at 80 Hz. The 80 Hz figure is a reasonable compromise, minimizing both the polarization errors present at low frequencies and severe cable length restrictions present at higher frequencies.

Refer back to FIGS. 2 and 3 and Equation 5. The conductivity measurement described here would apply the simple equation:

$$\rho = \frac{\overline{V_0} R_{REF}}{K(V_{IM} - \overline{V_0})} \qquad \text{Eq. 6}$$

to determine the solution's conductivity. This yields the correct result provided $C_E$ is not a significant factor. In cases where $C_E$ is significant, the error term of Equation 5 causes the system's measured $\overline{V_0}$ value to be too high, and hence the system's calculated solution resistivity is also too high.

For example, take the above-described system, operating at 80 Hz with a $K=0.01$ constant cell measuring solution at resistivity $\rho=10$ megohm-cm. A titanium-palladium electrode in the early stages of fouling could easily exhibit a $C_E$ value of 0.1 microfarads. Applying these numbers to Equations 5 and 6 shows an error of approximately three percent due to the electrode solution interface capacitance $C_E$. This is, of course, in addition to any basic measurement errors already present in the system.

Consider again Equation 5, which governs the voltage which the center-sampling measurement system will measure across the conductivity cell. Though complex, Equation 5 is a function of only five variables, all of which are either controlled or measured by the system, with the exception of $C_E$. If the value of $C_E$ could be determined, its effect on the measurement could be calculated and eliminated.

Figure 5:
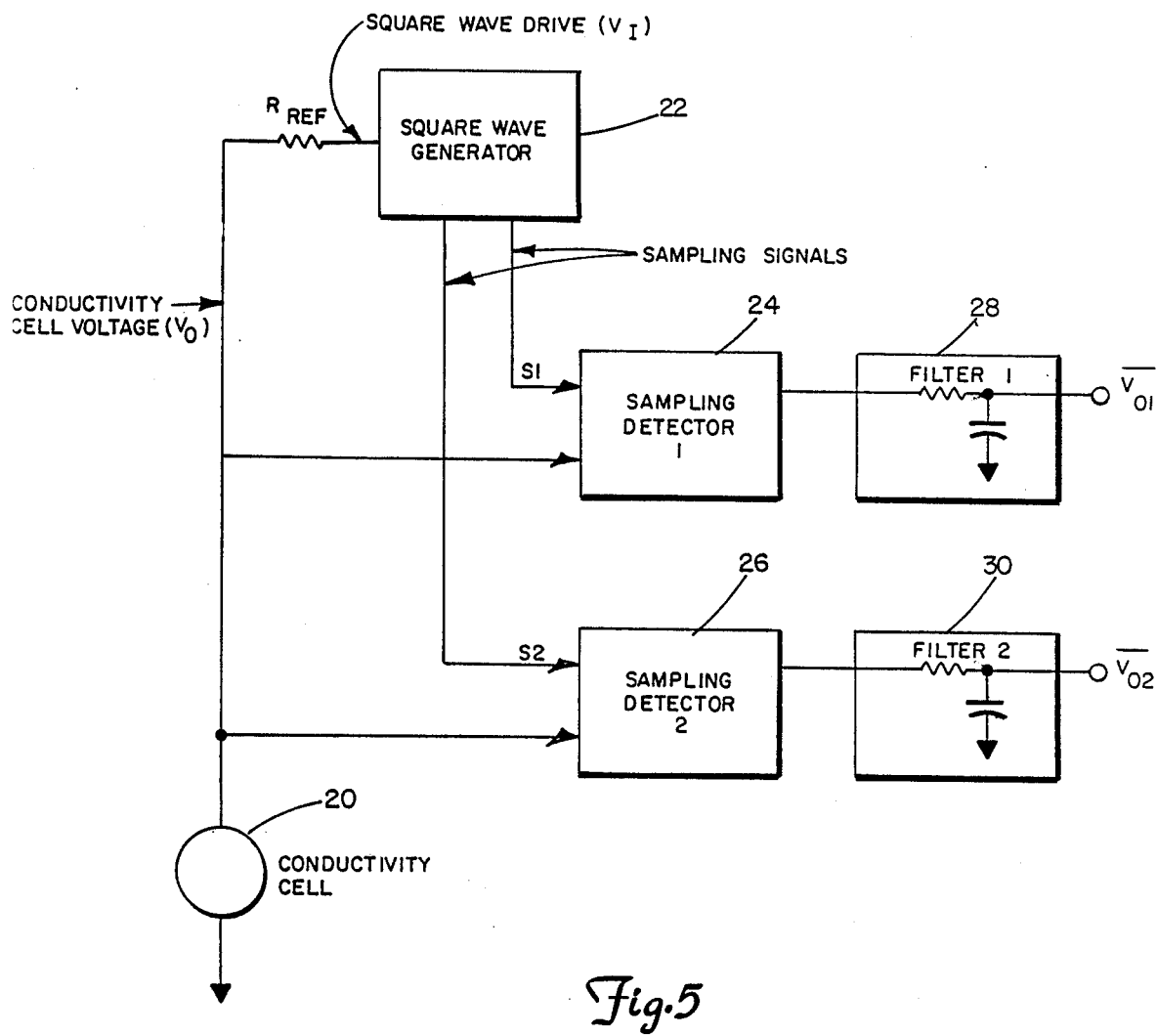
FIG. 5 is a block diagram showing an embodiment of the improved conductivity measurement system of the present invention.
Figure 6:
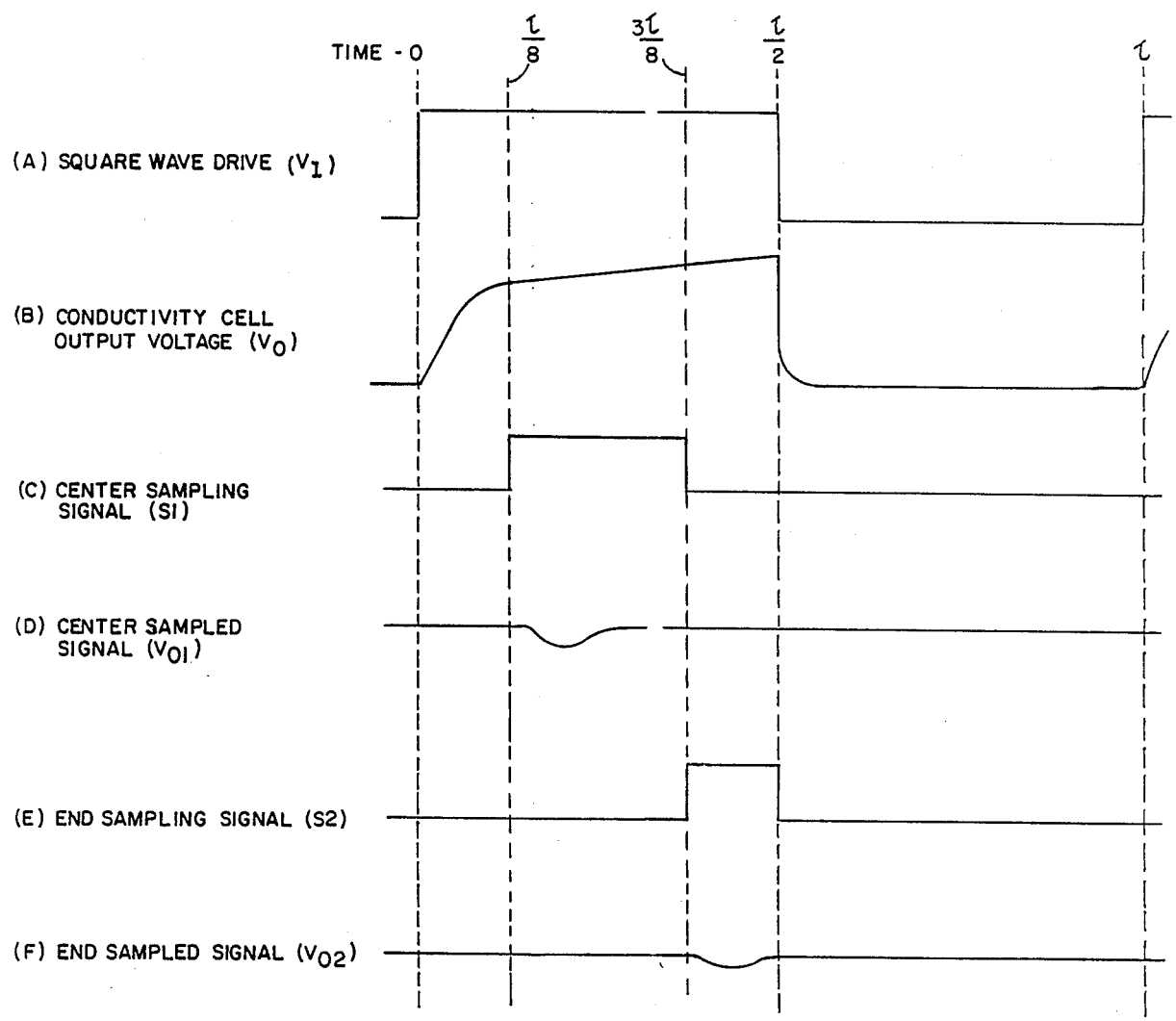
FIG. 6 shows waveforms produced by the measurement system of FIG. 5.

FIGS. 5 and 6 illustrate an improved system which produces signals from which a correction for the effects of $C_E$ can be made. In the block diagram shown in FIG. 5, conductivity cell 20 receives a square wave drive signal $V_I$ from square wave generator 22 through resistor $R_{REF}$. The conductivity cell voltage $V_0$ is supplied to two sampling detectors 24 and 26. Square wave generator 22 provides sampling signal S1 to sampling detector 24 and a second sampling signal S2 to sampling detector 26. As shown in FIG. 6, sampling signal S1 is a center-sampling signal which occurs between $\tau/8$ and $3\tau/8$, while sampling signal S2 is an end sampling signal which occurs $3\tau/8$ and $\tau/2$).

The output of sampling detector 24 is filtered by filter 28 to produce center-sampled signal $V_{01}$. Similarly, the output of sampling detector 26 is filtered by filter 30 to produce end sampled signal $V_{02}$.

In the system illustrated in FIGS. 5 and 6, the cell voltage $V_0$ is sampled over two independent windows during the positive half cycle. The cell output voltage measured during the two sample intervals $V_{01}$ and $V_{02}$ will differ because of $C_E$. Hence, the difference between the two measured voltage samples $\Delta V$ may be derived as:

$$\Delta V = V_{02} - V_{01} \qquad \text{Eq. 7}$$

$$\Delta V = \frac{2V_{IM}R_{REF}C_E}{1 + e^{\frac{-1}{2/C_E(R_C+R_{REF})}}} \times$$

$$\left[\frac{e^{\frac{-\tau}{8C_E(R_C+R_{REF})}} - e^{\frac{-3\tau}{8C_E(R_C+R_{REF})}}}{(\tau 14)} - \right.$$

$$\left. \frac{e^{\frac{-3\tau}{8C_E(R_C+R_{REF})}} - e^{\frac{-\tau}{2C_E(R_C+R_{REF})}}}{(\tau/8)} \right]$$

Note that all variables in Equation 7 are either known or measured with the exception of $C_E$. Thus Equation 7 may be used to calculate the value for $C_E$ which may then be used to eliminate the error term in Equation 5, thus improving the accuracy of solution conductivity calculation.

Two problems have yet to be discussed. The first is that Equation 7 requires the cell impedance $R_C = K \times \rho$ as a variable, so that $R_C$ must first be calculated from Equation 6 and will have a $C_E$ induced error component. Equation 7 is only slightly
nent. Equation 7 is only slightly perturbed by small errors ($\leq 5\%$) in $R_C$, however, and subsequent iterations of the process reduce even this error.

The major remaining problem is that Equation 7 is not readily solved for $C_E$, and iterative solution techniques are beyond the speed and memory limits of a small microcomputer of the type which would be cost effective in a conductivity measurement instrument.

To simplify the correction process to the point where it can be effectively handled by a small microcomputer-based instrument in real time, the information contained in Equations 7 and 5 are fitted to a second order polynomial. Commercially available curve-fitting programs serve the purpose adequately.

The sequence for deriving the $C_e$ error correction polynominal is as follows:

First note that Equation 7 gives the sampled voltage difference $\Delta V$ as a function of $C_E$. Next note that the second term of Equation 5 gives the calculated resistivity error as a function of $C_E$. Both equations also employ $R_C$ as a variable.

Combining the Error Term of Equation 5 with Equation 7, a family of curves, Calculated Resistivity Error v. Sampled Voltage Difference ($\Delta V$) for various values of $R_C$, is generated. A typical curve set is shown in FIG. 7.

Figure 7:
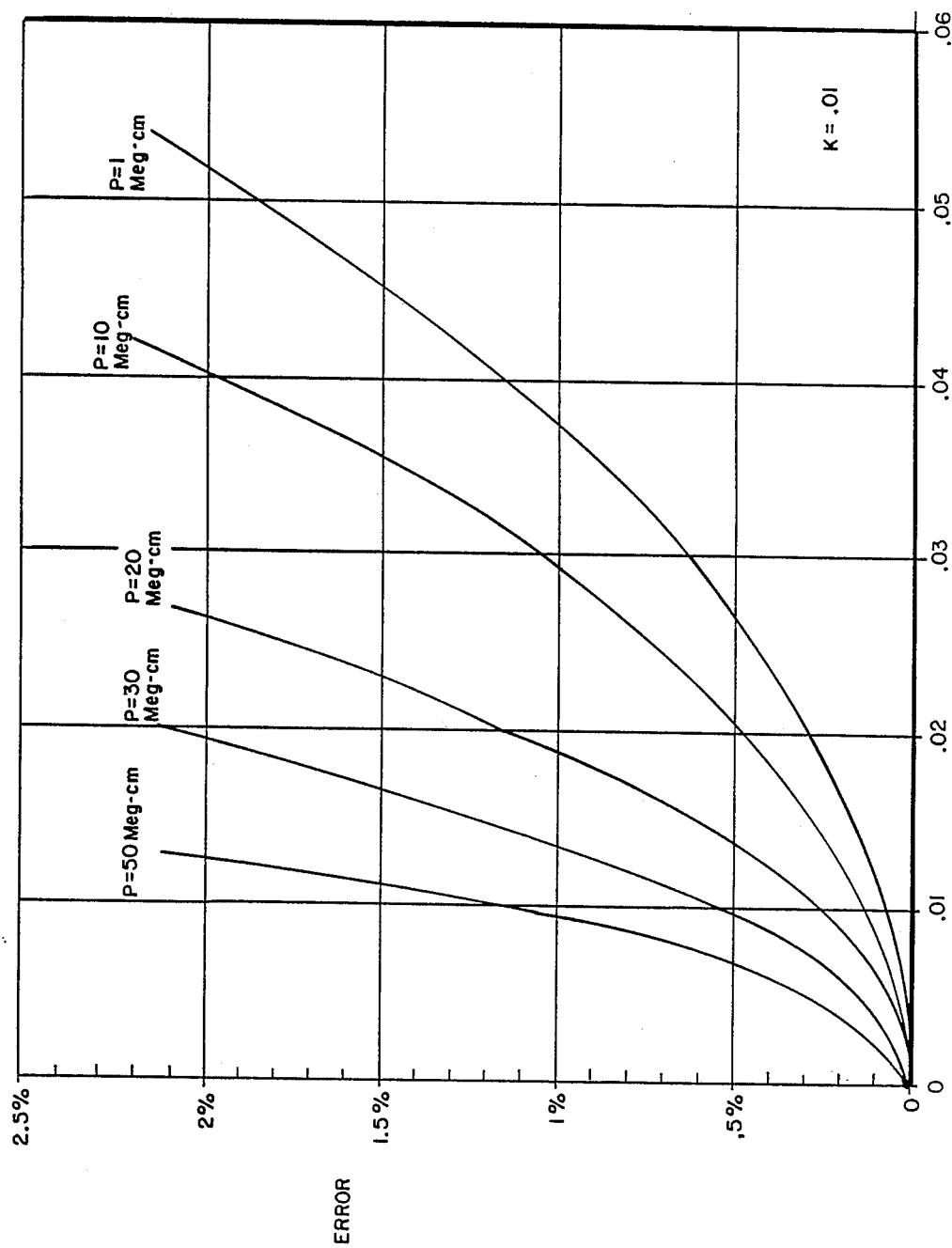
FIG. 7 is a graph showing resistivity error as a function of the difference in voltage between center-sampled and end-sampled signals.

As a final step, the data graphed in FIG. 7 is reduced to a polynomial expressing conductivity measurement system output error as a function of $\Delta V$ the difference between the cell output voltages measured over the two different sample windows in the drive waveform (S1 and S2 of FIG. 6). Note that $C_E$ need not be directly calculated by the conductivity measurement system. Rather, the difference in sampled voltages $\Delta V$ caused by $C_E$ is measured and used in the correction equation polynomial.

The following example is generated for the system modeled in FIG. 5 with the electrode modeled as in FIG. 4. The following component values apply:

$R_{REF} = 50,000$ ohms
$K = 0.01$

Curve fitting Equations 7 and 5 yield the correction term E such that:

$$E = 1 + (1.107 \times 10^{-2} + 3.85 \times 10^{-7} \times R_C) \times \Delta V - 7.7\text{-}3 + 5.88 \times 10^{-10} \times R_C^2) \times (\Delta V)^2 \qquad \text{Eq. 8}$$

Now the solution resistivity may be more accurately calculated as:

$$\rho = \frac{V_{01}R_{REF}}{K(V_I - V_{01})} \times E \qquad \text{Eq. 9}$$

Note again that this curve fit technique does not calculate the value for $C_E$ directly, but rather the $C_E$ induced error correction factor E. Because Equation 8 is only a second order polynomial equation, it does not perfectly represent Equations 7 and 5. Rather it is calculated to produce a "best approximation" over the intended measurement range for any given instrument. For the measurement example described above, application of Equations 8 and 9 successfully reduce $C_E$ induced errors in solution resistivity as great as five percent to less than one percent of the range 5 Meg-cm $\leq \rho \leq$ 50 meg-cm.

Figure 8:
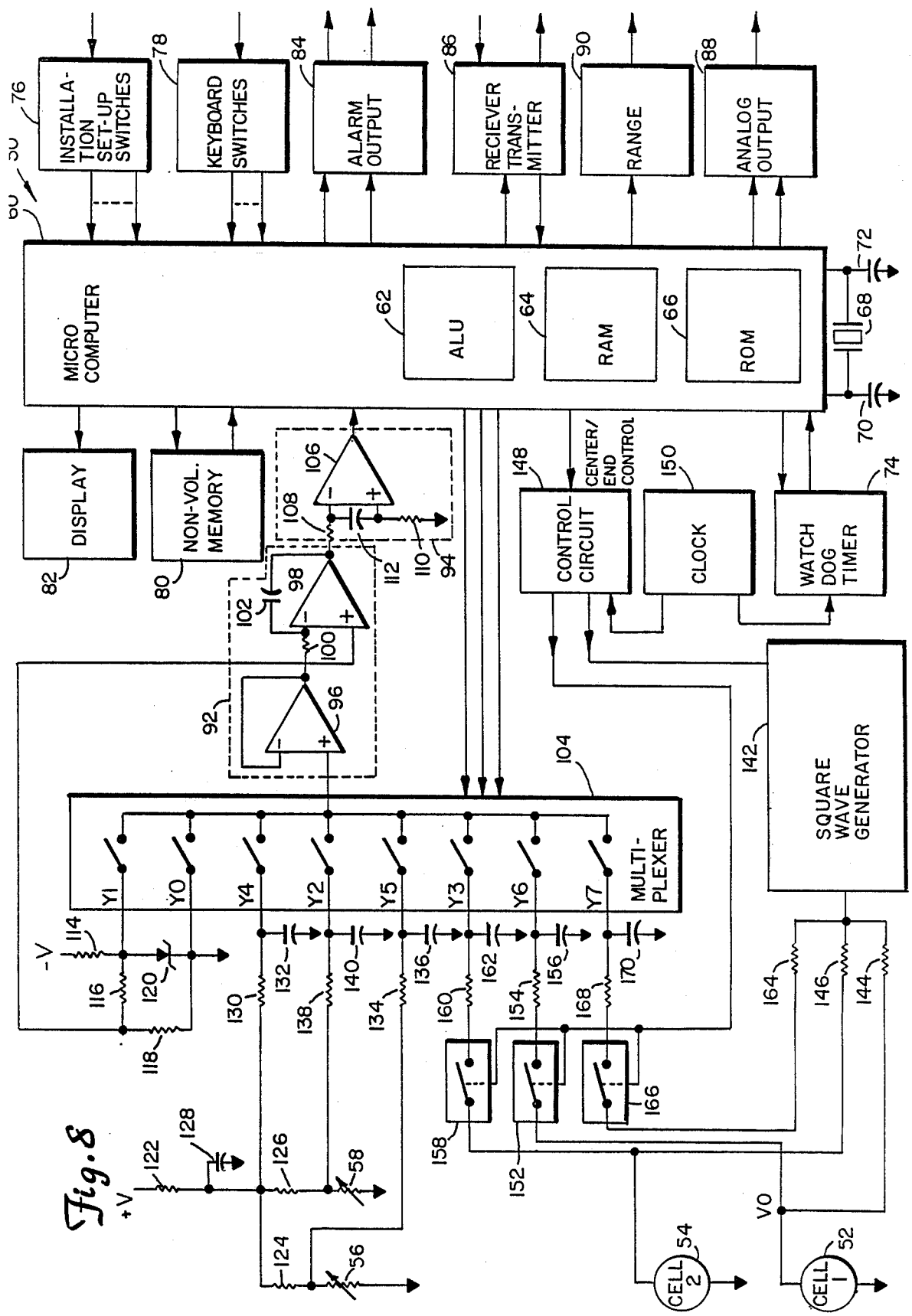
FIG. 8 is an electrical block diagram of a solution conductivity sensing system using the present invention.

FIG. 8 shows a conductivity measurement system 50 which embodies the present invention. A pair of conductivity cells 52 and 54 are used to measure solution conductivity. Associated with cell 52 is a RTD temperature sensor 56. Similarly, RTD 58 is associated with cell 54. Signals from RTD 56 and 58 provide temperature correction for the measured conductivity measured by conductivity cells 52 and 54, respectively.

The operation of system 50 is controlled and coordinated by microcomputer 60 which, in one embodiment, is a single chip microcomputer such as an Intel 8051. Microcomputer 60 includes arithmetic logic unit (ALU) 62, random access memory (RAM) 64, and read only memory (ROM) 66, along with associated input/output and control circuitry. Crystal 68 and capacitors 70 and 72 establish the clock reference for microcomputer 60.

Watchdog timer 74 is coupled to microcomputer 60 to provide a reset signal when microcomputer 60 fails to operate normally.

Installation setup switches 76 provide input signals to microcomputer 60 to provide various setup constants and parameters selected by the user. These include, for example, baud rate for communication to and from system 50, display of either conductivity or resistivity, selection of a current output mode, and calibration constants. Also providing input signals to microcomputer 60 are keyboard switches 78, which permit numerical values to be entered into microcomputer 60 and stored for later use.

Nonvolatile memory 80 is a nonvolatile random access memory which stores data such as calibration constants, alarm set points and the like during periods when conductivity measurement system 50 is deenergized.

System 50 provides outputs in a number of different forms. Display 82 is controlled by microcomputer 60, and displays data representing the measurements which have been made (as corrected by microcomputer 60). Other outputs are provided through alarm output 84, receiver/transmitter 86, analog output circuit 88, and range output circuit 90.

When certain limits of resistivity or conductivity have been exceeded, microcomputer 60 energizes alarm output circuit 84 to provide an alarm signal.

Receiver/transmitter 86 receives data and provides it to microcomputer 60 and also transmits data provided to it from microcomputer 60. In a preferred embodiment, receiver/transmitter 86 provides an RS232 interface between system 50 and other digital devices and systems.

Analog output circuit 90 provides an analog signal which represents measured conductivity or resistivity (either as an analog voltage or an analog current). Range output circuit 88 provides an indication of the range of conductivity (or resistivity) represented by the analog output.

The remaining circuitry shown in FIG. 8 provides the measured signals from which microcomputer 60 derives conductivity or resistivity value. The conductivity cells 52 and 54 and RTDs 56 and 58 produce analog signals which must be converted to digital form so that they can be processed by microcomputer 60. The conversion of analog signals to digital signals is achieved by a dual integrating ramp analog-to-digital (A/D) converter formed by integrator 92, comparator 94 and microcomputer 60. Integrator 92 includes op amps 96 and 98, resistor 100 and capacitor 102. The input signal to integrator 92 is received from multiplexer 104, which selects one of eight analog inputs based upon control signals from microcomputer 60. The output of integrator 92 is provided to comparator 94, which includes op amp 106, resistors 108 and 110, and capacitor 112.

The dual slope A/D converter first samples the analog signal which is to be converted for a predetermined period of time, and integrator 92 ramps in a first direction during that first time period. At the end of the first time period, microcomputer 60 causes multiplexer 104 to select a reference potential, and that reference potential is provided to the input of integrator 92. This causes the integrator 92 to ramp in a second, opposite direction. During the first time period in which the output of integrator 92 is ramping in the first direction, microcomputer 60 is counting clock pulses. When the output of integrator 92 reaches a predetermined threshold value, which is determined by comparator 94, the output of comparator 94 changes state. This causes microcomputer 60 to stop counting. The digital count which is obtained is a measure of the length of the first time period. Since the second time period is of fixed duration and the integrator output is a known value at the end of that second time period, the count of clock pulses during the first time period represents the magnitude of the analog signal presented to integrator 92 by multiplexer 104 during that first time period. The first and second time periods are repeated cyclically.

There are eight inputs (labeled Y0–Y7) to multiplexer 104. The signal at input Y1 is a negative reference voltage produced by a reference circuit formed by resistors 114, 116 and 118 and Zener diode 120. The reference circuit also provides a reference signal to the noninverting (+) input of op amp 98 of integrator 92.

Input Y0 is connected to ground, and therefore provides a ground reference potential.

RTD 56 and RTD 58 are connected in the energizing circuit which includes resistor 122, 124 and 126 and capacitor 128. A signal from the junction of resistor 122 with resistors 124 and 126 is a reference signal which is filtered by resistor 130 and capacitor 132 to provide an input reference signal at input Y4 of multiplexer 104.

The voltage across RTD 56 is provided to a filter formed by resistor 134 and capacitor 136 and is provided to input Y5 of multiplexer 104. Similarly, the voltage across RTD 58 is filtered by resistor 138 and capacitor 140 and provided to input Y2 of multiplexer 104.

Multiplexer 104 receives a filtered reference signal at its Y7 input, a filtered conductivity cell voltage of cell 52 at its Y6 input, and a filtered conductivity cell voltage of cell 54 at its Y3 input.

The drive to cells 52 and 54 is provided by square wave generator 142 through resistor 144 to cell 52 and through resistor 146 to cell 54. Square wave generator 142 is triggered by control circuit 148, which in turn receives clock signals from clock 150 and a center/end control signal from microcomputer 60.

The output voltage from cell 52 is supplied through switch 152 to a filter formed by resistor 154 and capacitor 156. The filtered signal is supplied to the Y6 input of multiplexer 104.

Similarly, the output voltage of cell 54 is provided to switch 158. The output of switch 158 is filtered by resistor 160 and capacitor 162. The filtered output voltage of cell 54 is provided to the Y3 input of multiplexer 104.

The reference signal from square wave generator 142 is provided through resistor 164 to switch 166. The output of switch 166 is filtered by resistor 168 and capacitor 170 and provided to the Y7 input of multiplexer 104.

The control terminals of switches 152, 158 and 166 are controlled by control circuit 148. In this way, sampling of the output voltages of cells 52 and 54 and sampling of the reference signal is controlled by control circuit 148.

For simplicity, the sampling of the output voltage of cell 52 will be described. The operation of system 50 in sampling signals from cell 54 is similar and will not be described separately.

Figure 9:
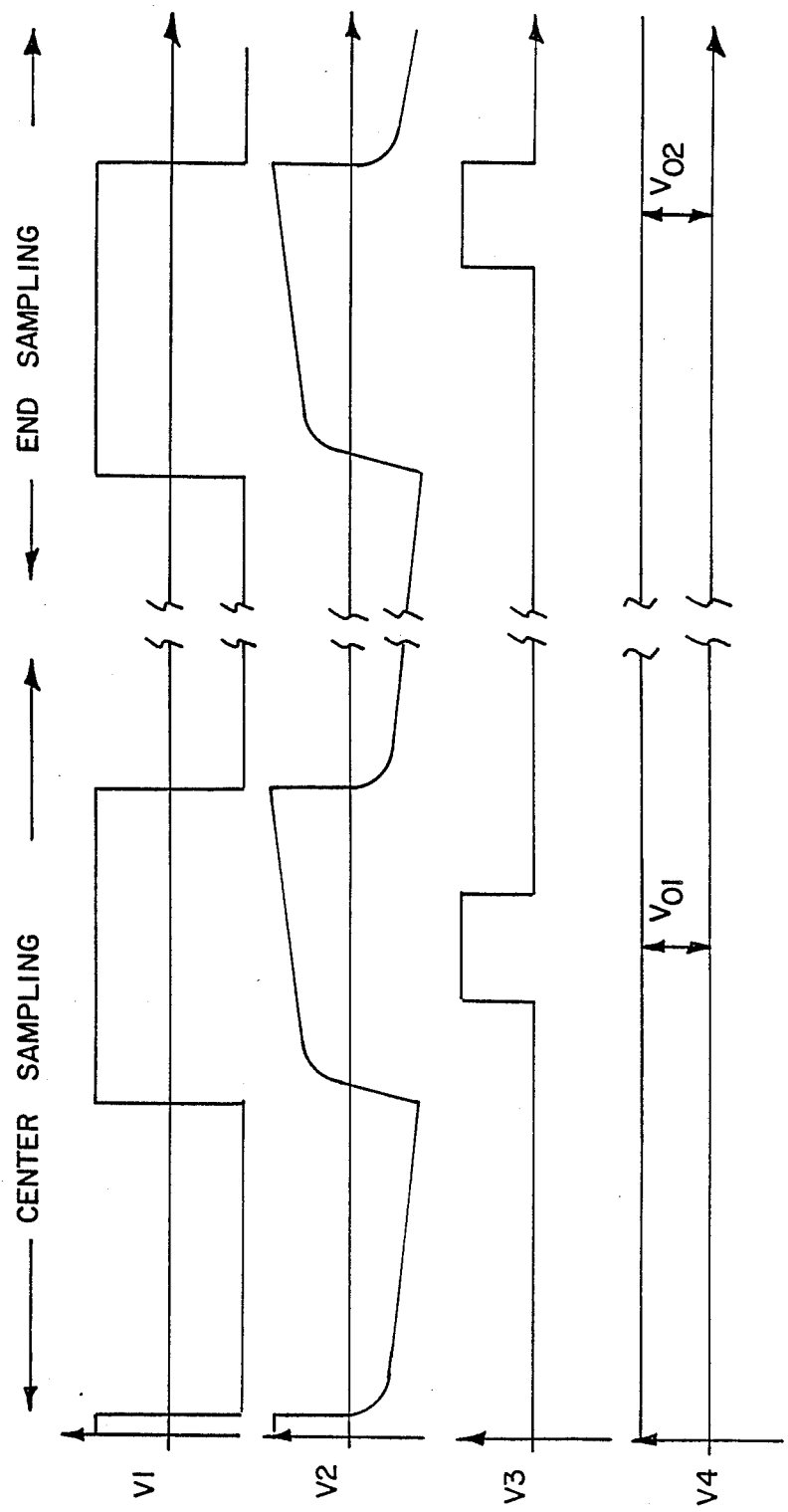
FIG. 9 shows waveforms produced by the system of FIG. 8.

As shown in FIG. 9, the output $V_1$ of square wave generator 142 is an AC square wave signal. The output voltage $V_0$ from cell 52 is also shown in FIG. 9. Control circuit 148 provides the sampling signal $V_3$ to the control terminals of switches 52, 58 and 166. During a first center-sampling period of operation, the sampling signal is centered in the center of the positive half cycle of the drive signal as shown in FIG. 9. The resulting voltage $V_{01}$ which appears at input terminal Y6 of multiplexer 104 represents the filtered voltage produced by center sampling of the cell output voltage $V_0$.

Periodically, microcomputer 60 causes control circuit 108 to change the sampling signal from a center-sampling signal to an end-sampling signal. When this occurs, the sampling signal is delayed until the latter end of the positive half cycle of the drive signal, as also shown in FIG. 9. The filtered voltage $V_{02}$ which appears as a result of end-sampling is provided to multiplexer 104.

Microcomputer 60 periodically causes the signal $V_{01}$ produced by center-sampling to be converted to a digital value and, similarly, causes the voltage $V_{02}$ produced by end-sampling to be converted to a digital value.

In addition, microcomputer 60 periodically causes the reference signal derived from the square wave drive (which appears at input terminal Y7) to be sampled, along with the temperature signal which appears at input terminal Y5, the reference signal which appears at Y4, and the reference signal which appear at Y0 and Y1. The reference signals provide calibration used by microcomputer 60 to scale the temperature and cell conductivity signals.

The temperature signal is used for temperature compensation of the cell conductivity signals, since the conductivity of the solution is a function of temperature.

From the center-sampled voltage $V_{01}$ and the end-sampled voltage $V_{02}$, which are converted to digital values by the A/D converter, microcomputer 60 calculates the appropriate error correction as shown in Equation 8 and then corrects the resistivity using that error correction as shown by Equation 9. The resulting corrected conductivity or resistivity value is then provided by microcomputer 60 to appropriate output devices such as display 82, analog output circuit 88, and receiver/transmitter 86. Microcomputer 80 also compares the corrected value with preset limits, and actuates alarm output circuit 84 as appropriate.

The enhanced center- and end-sampling conductivity measurement system of the present invention has been found to be particularly advantageous for industrial-type conductivity cells in high purity water applications. The present invention, however, is not limited to high purity water applications alone, but rather applies to contact-type conductivity measurements of all ranges. This includes systems measuring conductivity in order to calculate secondary variables such as acid, base or salt concentration, and conductivity measurements in nonaqueous solutions. In all of these cases, the component values in the conductivity cell model will change, and the form of curve fit equation (Equation 8) will change, but the basic method for elimination of electrode-solution interface capacitance still applies.

Figure 10:
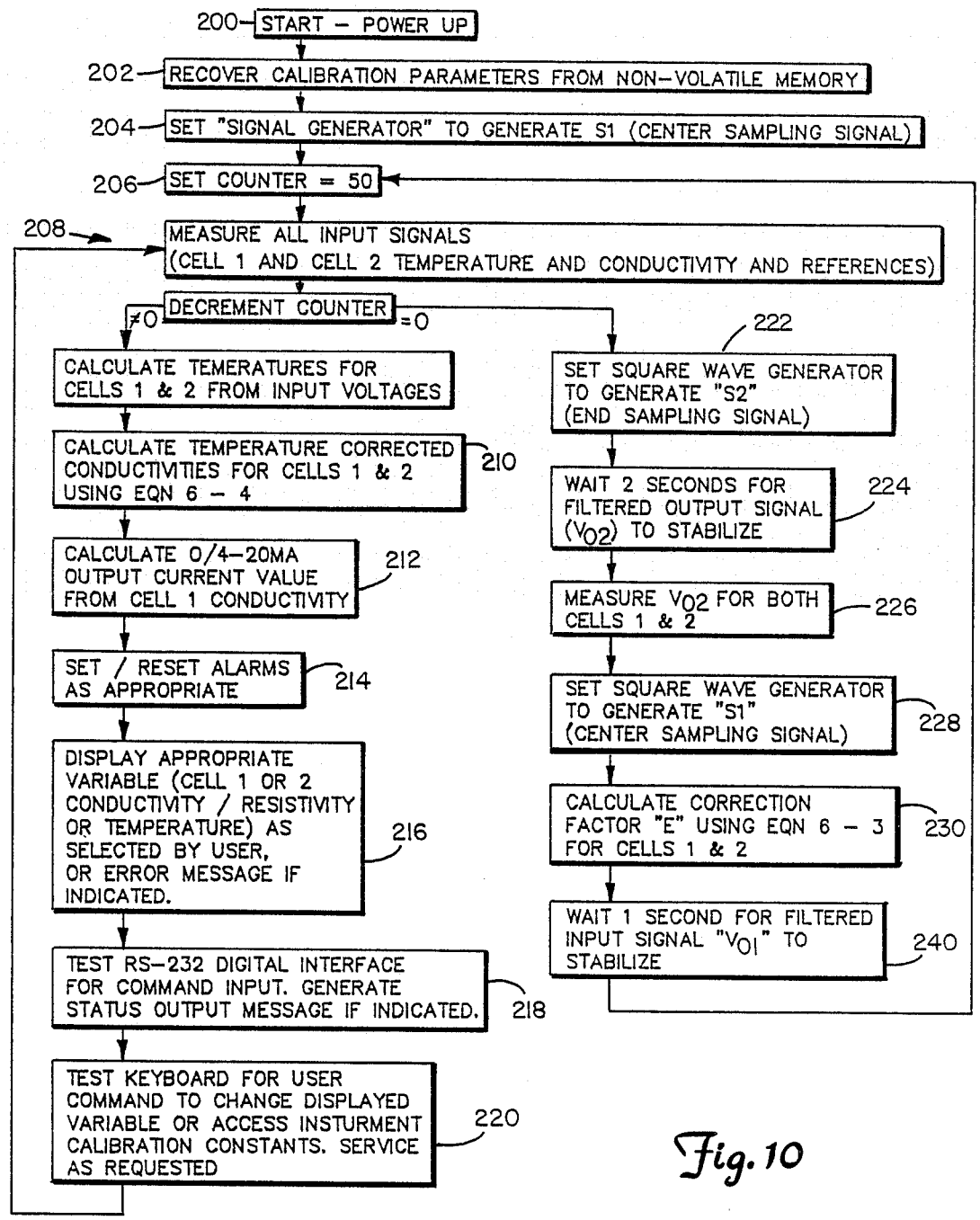
FIG. 10 is a flow diagram of the microcomputer of FIG. 8.

In FIG. 10, a flow chart shows the sequencing of operation of a conductivity sensing system such as shown in FIG. 8. After start or power up 200, the microcomputer system recovers calibration constants from the nonvolatile memory as shown at 202 and sets the sampling signal "V3" to perform center-sampling as shown at 204. A counter in the microcomputer is set to an initial setting of 50 as shown at 206 and then the microcomputer controls the multiplexer and the A/D converter to make fifty consecutive measurements of all of the analog inputs to the multiplexer, with the center-sampling being done on all the measurements from the conductivity cells as shown in the loop 208 on the left side of the flow chart in FIG. 10. During each of the fifty passes through loop 208, temperature correction is made as shown at 210, the analog output is updated as shown at 212, alarm outputs are updated as shown at 214, the display is updated as shown at 216, the receiver/transmitter is polled for messages as shown at 218, and the keyboard is polled as shown at 220 for user commands. At the end of fifty passes, the microcomputer system sets the sampling signal "V3" to perform end-sampling as shown at 222. After a wait for the end-sampled signal to stabilize at 224, end-sampling is done for both conductivity cells as shown at 226. The sampling signal is then set back to provide center-sampling as shown at 228, and the correction for capacitive effects is calculated as shown at 230. There is then a wait for the input signals to stabilize as shown at 240 and then the system returns to the main measurement loop 208. The correction factor calculated at 230 is used in the main measurement loop 208 for correcting conductivity or resistivity displays and outputs for capacitive effects.

Although the present invention has been described with reference to preferred embodiments, workers skilled in the art will recognize that changes may be made in form and detail without departing from the spirit and scope of the invention.

What is claimed is:

1. A circuit for providing an output representative of a conductivity sensed by a cell which produces a cell signal which is affected by a capacitance, comprising:
    excitation means coupled to the cell for providing time-varying excitation to the cell;
    sampling means coupled to the cell for sampling the cell signal during first and second different time intervals wherein the sampling performed during the first and second different time intervals is of time duration less than a half cycle of the time-varying excitation; and
    measurement means coupled to the sampling means for measuring the cell signal as sampled during the first and second time intervals and providing the output substantially corrected for the effect of the capacitance.

2. The circuit of claim 1 wherein the measurement means measures a magnitude of the cell signal sampled during the first time interval and a magnitude of the cell signal sampled during the second time interval.

3. The circuit of claim 2 wherein the measurement means computes the correction as a function of the magnitudes of the cell signal sampled during the first and second time intervals.

4. The circuit of claim 3 wherein the sampling means comprises at least one switch controlled to conduct during the first time interval.

5. The circuit of claim 1 wherein the excitation is substantially a square wave waveform.

6. The circuit of claim 5 wherein the first time interval is a center-sampling interval within a half cycle of the square wave waveform.

7. The circuit of claim 5 wherein the second time interval is an end-sampling interval within a half cycle of the square wave waveform.

8. The circuit of claim 7 wherein the measurement means comprises an integrating ramp analog-to-digital converter.

9. The circuit of claim 8 further comprising:
temperature sensing means coupled to the cell for sensing a temperature of the cell and providing a signal representative of temperature to the measurement means; and
wherein the measurement means corrects the output for an effect of temperature.

10. A method of measuring conductivity of a fluid with a conductivity cell, the method comprising:
applying an AC drive signal to the cell;
sampling an output of the cell during a first time interval of duration less than a half cycle of the AC drive signal to produce a first cell signal;
sampling the output of the cell during a second, different, time interval of duration less than a half cycle of the AC drive signal to produce a second cell signal;
deriving a correction for capacitance induced error based upon the first and second signals; and
producing an output representative of measured conductivity based upon the first cell signal and the correction.

11. The method of claim 10 wherein the first time interval occurs in a center portion of a half cycle of the AC drive signal.

12. The method of claim 11 wherein the second time interval occurs in a portion of the half cycle different at least in part from the center portion.

13. The method of claim 10 wherein the AC drive signal has a square wave waveform.

14. A method of measuring conductivity of a fluid with a conductivity cell, the method comprising:
applying a time-varying drive signal to the cell;
sampling an output of the cell during first and second time intervals in which the output differs due to electrode-solution interface capacitance, wherein each of the first and second time intervals is of a time duration less than a half cycle of the time-varying drive signal;
producing an output representative of measured conductivity based upon the sampled output of the cell and corrected for effects of the electrode-solution interface capacitance in the output of the cell.

* * * * *

UNITED STATES PATENT AND TRADEMARK OFFICE
CERTIFICATE OF CORRECTION

PATENT NO. : 4,808,930

DATED : February 28, 1989

INVENTOR(S) : Donald F. Kaiser

It is certified that error appears in the above-identified patent and that said Letters Patent is hereby corrected as shown below:

In the ABSTRACT, line 2, delete "measurment" and insert "measurement"

Column 4, line 56, delete "Works", insert "works"

Column 6, line 17, delete " $\tau/8$ to $\tau 8.$ " and insert " $\tau/8$ to $3\tau/8.$ "

Column 7, line 45, delete " $\overline{(\tau I 4)}$ " and insert " $\overline{(\tau/4)}$ "

Column 7, line 62, delete "nent. Equation is only slightly"

UNITED STATES PATENT AND TRADEMARK OFFICE
CERTIFICATE OF CORRECTION

PATENT NO. : 4,808,930

DATED : February 28, 1989

INVENTOR(S) : Donald F. Kaiser

It is certified that error appears in the above-identified patent and that said Letters Patent is hereby corrected as shown below:

Column 8, line 40, delete Equation 8 and insert $$E = 1+(1.107 \times 10^{-2}+3.85 \times 10^{-7} \times R_C) \times \Delta V$$
$$-(7.735+5.88 \times 10^{-10} \times R_C^2) \times (\Delta V)^2 \qquad \text{Eq. 8}$$

Signed and Sealed this

Eighth Day of August, 1989

Attest:

DONALD J. QUIGG

Attesting Officer

Commissioner of Patents and Trademarks